United States Patent [19]
Orlando et al.

[11] Patent Number: 5,141,329
[45] Date of Patent: Aug. 25, 1992

[54] MICRO FREEZE POINT ANALYSIS APPARATUS AND METHOD

[75] Inventors: Thomas W. Orlando; Vincent T. Randal, both of San Antonio, Tex.

[73] Assignee: Alcor, Inc., San Antonio, Tex.

[21] Appl. No.: 589,376

[22] Filed: Sep. 27, 1990

[51] Int. Cl.$^5$ ............................................. G01N 25/04
[52] U.S. Cl. ...................................... 374/16; 374/25; 364/557
[58] Field of Search ................... 374/16, 25, 102, 104, 374/107; 364/557 X

[56] References Cited

U.S. PATENT DOCUMENTS

| | | | |
|---|---|---|---|
| 2,922,304 | 1/1960 | Lees et al. | 374/25 |
| 3,250,115 | 5/1966 | Donnell | 73/17 |
| 3,267,728 | 8/1966 | Solomons | 73/190 |
| 3,319,457 | 5/1967 | Leone | 73/17 |
| 3,360,993 | 1/1968 | MacMillan | 374/25 |
| 3,504,525 | 4/1970 | Ishii | 73/17 |
| 3,518,838 | 7/1970 | Newton | 62/3 |
| 3,667,280 | 6/1972 | Simpson | 374/25 |
| 3,677,064 | 7/1972 | Simpson | 374/25 |
| 3,695,093 | 10/1972 | Hummel et al. | 73/17 R |
| 4,046,509 | 9/1977 | Bäckerud | 374/25 |
| 4,383,770 | 5/1983 | Boschung et al. | 364/557 X |
| 4,564,900 | 2/1971 | Andre et al. | 73/17 |
| 4,601,587 | 7/1986 | Mathiprakasam | 374/25 |
| 4,760,538 | 7/1988 | Bock et al. | 364/557 |

FOREIGN PATENT DOCUMENTS

| | | | |
|---|---|---|---|
| 163552 | 9/1984 | Japan | 374/16 |
| 44852 | 3/1985 | Japan | 374/16 |
| 763755 | 9/1980 | U.S.S.R. | 374/25 |
| 1286974 | 7/1985 | U.S.S.R. | 374/25 |
| 1176907 | 1/1970 | United Kingdom . | |
| 2032102 | 4/1980 | United Kingdom | 374/16 |

OTHER PUBLICATIONS

NASA document CR-167981, by B. Mathiprakasam, Contract NAS 3-22543, Sep., 1982.
NASA document CR-168305, by B. Mathiprakasam, Contract NAS 3-22543, final report, Feb. 9, 1984.

Primary Examiner—William A. Cuchlinski, Jr.
Assistant Examiner—G. Bradley Bennett
Attorney, Agent, or Firm—Gunn, Lee & Miller

[57] ABSTRACT

An apparatus and method for determining the freezing point of substances, particularly liquids, that are likely to be used in environments that subject them to temperatures at or near their freezing points. The apparatus and method achieve a determination of the freezing point of the substance without the necessity of rigidly controlling the warming and cooling of the substance and without mistaking errant fluctuations in the thermal behavior of the substance for the freezing point. The apparatus includes a test sample cell that is cooled by direct contact with a rapidly expanding gas and a means for recording and analyzing temperature and time data for a test sample within the test sample cell. Means for controlling the test and displaying the information/data are also provided. The method utilizes a numerical analysis means to arrive at a freezing point value without the necessity of complex differentiating electronics or calculations. The method is capable of ignoring anomalies in the thermal characteristics of the substance and isolating the characteristics which are indicative of the freezing point. The apparatus and method can be packaged in a small, compact configuration that is portable and battery powered.

12 Claims, 5 Drawing Sheets

MICRO FREEZE POINT ANALYSIS APPARATUS AND METHOD

BACKGROUND OF THE INVENTION

A. Field of the Invention:

The present invention relates generally to devices and methods for measuring the freezing points of liquids. The present invention relates more specifically to an apparatus and a method for measuring the freezing point of liquids by employing a very small sample of a liquid and by numerically analyzing the thermal characteristics of the liquid.

B. Description of Related Art:

Whenever a substance is utilized in an environment that potentially allows for the substance to change phase, an accurate knowledge of this phase change would be desirable in order to control the effects this phase change might have on the performance of the substance. Systems that are designed to handle liquids, for example, frequently experience difficulties when the liquids change over to the gaseous state and yet continue to be contained and handled by mechanisms designed for liquids. Similarly, when a system is designed to handle liquids and the possibility exists that these liquids could solidify, a concern for the point at which solidification beings to occur and the effects that solidification has on the system becomes important. An example of this concern can be seen in the aircraft industry where the presence of low temperatures at high altitudes increase the potential for the freezing of hydrocarbon based fuels and lubricants.

The present invention is concerned with determining the point at which a substance changes phase between a liquid and a solid. Strictly speaking, the freezing point of a substance is defined as the temperature at which both liquid and solid may exist in equilibrium. In the real world, the concern for the freezing point of a substance begins when crystalline solids start to form, or finally disappear as the case may be, from the liquid phase of the substance. The "freezing point", therefore, that is of concern here is that point at which all solids have been transformed into liquids, when looking at a transition from the solid to the liquid phase, or the point at which solids begin to form, when looking at the transition from the liquid to the solid phase.

There are many methods for determining the point at which this liquid-solid phase change occurs. A number of physical properties of the substance can be measured which reflect the presence or absence of crystalline solids in combination with the liquid substance. The present invention is primarily concerned with a specific thermal technique for determining the presence or absence of these solids. An analysis of the way in which heat is absorbed or removed from the substance and the resultant temperature changes in the substance can provide an indication of the point at which crystals start to form, or finally disappear, in the liquid.

The change between a liquid and a solid can, of course, move in two directions. A liquid may solidify and a solid may liquify, both phase changes passing through the freezing point of concern here.

An analysis of these phase changes for the purposes of this invention directly involves measurements of time and temperature and indirectly involves an analysis of the heat flow in and out of the substance.

For a substance composed of a single compound, the heat flow and the changes in temperature with respect to time can be described and analyzed very simply. As such a substance is cooled while in the liquid state, heat is removed from the substance and flows into the surrounding environment. This heat flow out of the substance is reflected by a corresponding temperature decrease in the liquid.

The heat flow out of the substance during this cooling process is essentially the exchange of energy between the substance and the surrounding environment. In the first instance, over a temperature range above the freezing point of the substance, the energy flow out of the liquid reflects a decrease in the kinetic energy of the molecules in the liquid. This decrease in kinetic energy is measured as a decrease in the temperature of the liquid. At the freezing point of the substance, the energy exchange from the substance to the environment does not derive from a change in the kinetic energy of the molecules, but rather derives from the reorganization of the molecules in the substance into the crystalline lattice of a solid. The crystalline lattice structure of a solid allows the molecules to exist at a lower energy state. There is a net difference in energy between molecules existing in a liquid state at a given temperature and molecules existing in a solid state at that same temperature. As a "cooling" of the substance continues, more and more molecules are arranged in the crystalline lattice structure and release a corresponding amount of energy into the environment that is exhibited as a continued heat flow ("latent heat") out of the substance. Once all such liquid molecules have arranged themselves in the solid structure and have released a corresponding amount of energy as a result, then the continued cooling of the substance reverts back to a continued decrease in the kinetic energy of the molecules. This is reflected by a continued decrease in the temperature of the now solid substance.

The problem with examining and analyzing the phase change on the cooling curve described above is the phenomenon known as "supercooling" that occurs in a liquid prior to its phase change into the solid state. Supercooling occurs when the temperature continues to drop below the freezing point of the substance without any crystalline structures forming. Whether and to what extent a substance tends to supercool rather than undergo a phase change at its freezing point is often a function of the purity of the substance and the presence or absence of seed crystals or seed surfaces within the liquid.

The warming curve of a substance on the other hand is more appropriately and more accurately a source of determining the actual freezing point of the substance. In much the reverse of the cooling curve, a warming curve describes an energy or heat flow into the solid substance which corresponds to an increase in the temperature of the solid indicative of an increase in the kinetic energy of the molecules in the solid. At a certain point, the kinetic energy of the molecules is sufficient to break the crystalline lattice structure of the solid and allow the molecules to move freely in a liquid state. Once the energy flow into the substance initiates this phase change from the solid to the liquid state, the energy into the substance is no longer reflected by an increase in the temperature, but is reflected instead by the continued movement of molecules from the solid state to the liquid state. When the energy or heat input into the substance is sufficient to completely change all molecules from the solid state to the liquid state, then the continued flow of energy into the substance is again reflected by an increase in the temperature of the substance. The point at which this change occurs, the so called "knee of the curve", is the point at which the last molecules absorb energy from the environment and break themselves free from the crystalline lattice structure to exist in the liquid phase. It is this point at which the temperature of the substance begins to rise again in response to the continued flow of energy, that can readily be measured so as to determine the "melting point" of the substance, and in fact, does represent a characteristic point at which the crystalline form of the material no longer exists.

For a substance that is not a single compound, but rather is a mixture of various compounds, each with separate freezing points, an analysis of the critical temperature becomes more complicated. Rather than a sharp transition from a heat flow that results in a temperature change to a heat flow that results in the phase change, there is a gradual change over from one to the other. Therefore, as a mixture passes through the range of freezing points for its various components, some of the heat being exchanged with the environment reflects a temperature change and some of the heat reflects a phase change. It is therefore difficult to determine either the first point at which crystals begin to form in the liquid substance on the cooling curve, or the last point at which crystals exist in the substance on the warming curve. Such determinations require a more careful analysis of the rate of change of temperature rather than simply the identification of the point at which the temperature begins to change again. The "plateau" that clearly exists in the temperature curve of a pure substance, will typically be vague and undefined in the temperature curve of a mixture.

There have been many attempts in the past to provide devices and methods for determining the freezing points of liquid mixtures. Some of these methods focus on measurements associated with the cooling curve. The problems already described above with regard to the cooling curve have not entirely been eliminated, and more accurate and reliable measurements continue to be made with an analysis of the warming curve.

Attempts in the past to measure and analyze the warming curve have focused on determining an "inflection point" during which the rate of temperature change decreases, and then increases over a short time interval. The methods used in the past gather temperature data relative to time, as the substance is warmed, and use differentiators to determine an inflection point of the temperature curve. The first derivative, which is an indication of the rate of change of the temperature, can be determined and used to define the inflection point as a peak or valley in an otherwise smooth curve.

The problem with these methods, apart from the fact that they require electronic differentiators and generally require microprocessors that can handle first derivative analysis of the data, is that their results fail to coincide with the accepted standardized results obtained by methods specified by the American Society For Testing Materials (ASTM) Method Number D2386 and the Institute of Petroleum (IP) Method Number IP-16, which are identical and which are world wide accepted standard test methods. In theory, an accurate first derivative differentiation and perhaps a second derivative differentiation of the warming curve may produce a value closest to the true "freezing point". But the reality is that anyone concerned with the "freezing point" of a liquid in the real world, will want to make a determination of the freezing point that is in accord with the accepted standards. Therefore, while the careful and exacting analysis of many of the existing methods provide an interesting theoretical study, they do not provide the practical method that the real world user of such a device would require.

Apart from the shortcomings of the methods described above, the devices that have been designed to be used in association with these methods have a number of short comings in and of themselves. Basically, all of these devices, whether measurements are made on the cooling curve or on the warming curve, require some method of cooling a sample of liquid and then controllably rewarming the sample through the critical freezing point. For most substances of concern, the freezing point of the liquid is somewhere below room temperature and thus the devices that are used necessarily have cooling components which can reduce the temperature of the liquid sample below that of room temperature.

Cooling systems have never been simple or compact. In order to withdraw heat from a substance, the device must provide a large thermal reservoir that can be placed in contact with the substance and not rapidly become "saturated" with the heat that is drawn from the substance. If such a reservoir is to be a solid substance, as in the case with thermoelectric heat pumps, it must be of sufficient size to allow the rapid dissipation of the heat throughout its structure and not allow that area of its structure that is in contact with the substance to build up with the heat from the substance and thereby slow down the cooling. On the other hand, the use of liquids and gases to provide cooling can likewise involve significantly cumbersome mechanisms. Cooling systems that function with compressors (the typical principal upon which most commercial refrigeration systems function) require large amounts of energy to run, are usually large and heavy, and seldom are capable of rapidly cooling a substance to the low temperatures necessary in many applications.

There is a direct relationship between the size of the sample and the resultant size of cooling apparatus necessary to sufficiently reduce the temperature of the sample below its freezing point. Clearly, the smaller the sample that is required, the less cumbersome the cooling system that is necessary. On the other hand, it is important that the cooling system be sufficiently controllable as to allow for the accurate measurement of the freezing point, as it is passed, in a reasonable period of time. The problems associated with many of the previous attempts to control the warming and cooling of a substance in order to determine its freezing point, have frequently been associated with the bulky devices that are required for this controllable warming and cooling. Furthermore, the size of equipment can possibly preclude its use in today's busy and crowded laboratories where space is already a problem.

It would be advantageous to have a method and device which in combination can provide both procedural simplicity and structural compactness that is desirable, and still achieve an accurate determination of the freezing point that is in accord with accepted standards, all within the confines of more simplified cooling and warming controls. While large, elaborate warming and cooling systems might eliminate most of the undesirable influences of a testing environment and might accurately control warming rates, they have by experience created "overly exact" readings of the freezing point. If a method were found that could accurately measure the freezing point in accordance with acceptable standards and could do so with a device that was sufficiently compact and simple, then the proper balance between practicality and accuracy would be realized.

FIG. 4 in the drawing discloses a graph which describes in general terms the methods by which previous devices have most successfully attempted to determine the freezing point of certain typical petroleum liquid fuels. FIG. 4 is a graph of the relationship between two variables, x representing time on the horizontal axis, and T(x) representing relative temperature on the vertical axis. The primary curve disclosed in the graph is the solid line with intermittent dots. This curve represents a section of the warming curve for a fuel substance (i.e., a hydrocarbon mixture) passing from the solid state to the liquid state. Each dot on the warming curve represents a discrete data sample at a specific time interval. The duration of the specific time interval depends upon the degree of error desired in the determination of the freezing point. A vague plateau can be discerned near the center of the warming curve in FIG. 4. This plateau is indicative of a phase change from the solid to the liquid state, i.e., a portion of the substance is changing from solid to liquid. During the time interval over which the curve flattens out, the heat being input into the substance does not correspond to a temperature change, but rather is primarily the latent heat of melting that does into converting the substance from the solid to the liquid phase. The heat input into the substance continues to force the phase change until such time as all of the solid components of the substance have changed to liquid. Once the last solids become liquid the continued flow of heat into the substance once again forces a temperature change. The "freezing point" described above is the point at which the heat flow stops effecting a phase change and starts effecting a temperature change. Theoretically this is the same point at which the standardized methods detect when the last crystal melts.

Methods of determining the freezing point from the warming curve of a substance, have focused primarily on the differentiation of the curve in order to accurately determine the rate of change of the temperature of the substance and therefore the point at which the temperature starts changing again after the phase change. Some previous methods, such as that described in U.S. Pat. No. 4,601,587, issued to Mathiprakasan, utilize the first derivative of the warming curve to determine this "freezing point". The first derivative in FIG. 4 is indicated by the solid line labeled dT/dx. This first derivative, generally speaking, is indicative of the rate of change of the temperature with respect to time. This curve peaks at a point where the rate of change of temperature is high. This point is indicated by the letter A in FIG. 4. It is this value that is used to identify the so called "knee of the curve", and thereby to identify the freezing point temperature.

As mentioned in the above discussion, differentiation may in fact provide an accurate "freezing point" for a given substance. In reality however, the results of these methods have been shown to err by as much as two degrees centigrade from the results determined by the accepted standards in the industry. Industry standards obtain results that are closer to what is shown as the second derivative of the warming curve. The second derivative is shown as a dashed line in FIG. 4 and is labeled by d(dT/dx)/dx. The second derivative generally speaking is an indication of the rate of change of the rate of change of the temperature in the warming curve. As an analogy, if the first derivative is considered to be the speed of temperature change, the second derivative is the acceleration with which the temperature is changing. Therefore, though the temperature may be changing at a greater speed at point A, it is accelerating the greatest at point B. It is this peak "acceleration" in the temperature change that more accurately reflects the "freezing point" results of standardized methods.

The problem with utilizing the second derivative in determining the freezing point lies not only in the complexities of the calculations and the kinds of microprocessors necessary to make the determination, but also in the frequency of independent anomalies in the second derivative curve that could be mistaken for the actual freezing point. If these anomalies in the second derivative curve that could be mistaken for the actual freezing point. If these anomalies could be sufficiently reduced and/or eliminated, then it is conceivable that the second derivative could be a practical way of obtaining freezing point results that are in accord with the standardized tests.

The present invention will be shown to disclose an alternative to utilizing the first or second derivative to determine this freezing point. A unique numerical analysis method has been found to achieve much the same accuracy that the second derivative analysis achieves without the complexity and without the possibility for mistaking an anomaly for the freezing point. This method is described in more detail hereinbelow.

II. SUMMARY OF THE INVENTION

It is an object of the present invention to provide an apparatus and a method for determining the freezing point of liquids.

It is a further object of the present invention to provide an apparatus and a method for determining the freezing point of hydrocarbon fuel mixtures.

It is a further object of the present invention to provide an apparatus and a method for determining the freezing point of liquids that obtains results substantially in accord with results obtained by standard accepted methods.

It is a further object of the present invention to provide an apparatus and a method for determining the freezing point of liquids that can be integrated in a package that is portable and is capable of use in the field.

It is a further object of the present invention to provide an apparatus for determining the freezing point of a liquid that requires only a very small sample quantity of liquid.

It is a further object of the present invention to provide an apparatus for determining the freezing point of a liquid that utilizes the warming curve thermal characteristics of the liquid.

It is a further object of the present invention to provide an apparatus for determining the freezing point of a liquid that does not require finely calibrated control of either the cooling of the test sample or of the warming of the test sample.

It is a further object of the present invention to provide a method for determining the freezing point of a liquid that is capable of disregarding anomalies in the thermal characteristics of the warming curve that are not indicative of the freezing point of the liquid.

It is a further object of the present invention to provide a method for determining the freezing point of a liquid that does not rely on differentiating electronics and/or differential calculations.

It is a further object of the present invention to provide a method for determining the freezing point of a liquid that allows for such determination in a relatively short period of time.

It is a further object of the present invention to provide a method for determining the freezing point of the liquid that numerically analyzes the thermal characteristics of the warming curve by way of integer calculations.

In fulfillment of these and other objectives, the present invention discloses an apparatus and a method for determining the freezing point of a liquid that places a very small sample of the liquid in a test cell, and cools the sample to a temperature below a predicted freezing point by positioning the test cell in close proximity to a point at which a compressed gas is allowed to rapidly expand. The rapidly expanding gas quickly absorbs heat from the test cell and the liquid sample within it and reduces the sample to a temperature below an expected freezing point value. The apparatus includes a reservoir of compressed gas that is connected to the test cell and provides over pressure and bypass ports in the test cell that aid in the control of the gas expansion. The test cell incorporates a means whereby a test sample may be easily introduced and easily expelled from the cell. Once the sample has cooled below an expected freezing point the cooling gas is cut off and the test cell and sample are allowed to passively warm back through the expected freezing point. While warming occurs, periodic temperature data is taken and is compared to hypothetical linear warming temperature values. The point at which the last local maximum negative deviation of the temperature data from the linear temperature values occurs is determined to be the freezing point of the liquid.

A preferred embodiment of the present invention is described hereinbelow in detail with reference to the accompanying Figures. Further elements and embodiments of the present invention will become obvious in light of the description below and of the claims following therefrom.

III. BRIEF DESCRIPTION OF THE DRAWING

IV. DETAILED DESCRIPTION OF A PREFERRED EMBODIMENT

Figure 1:
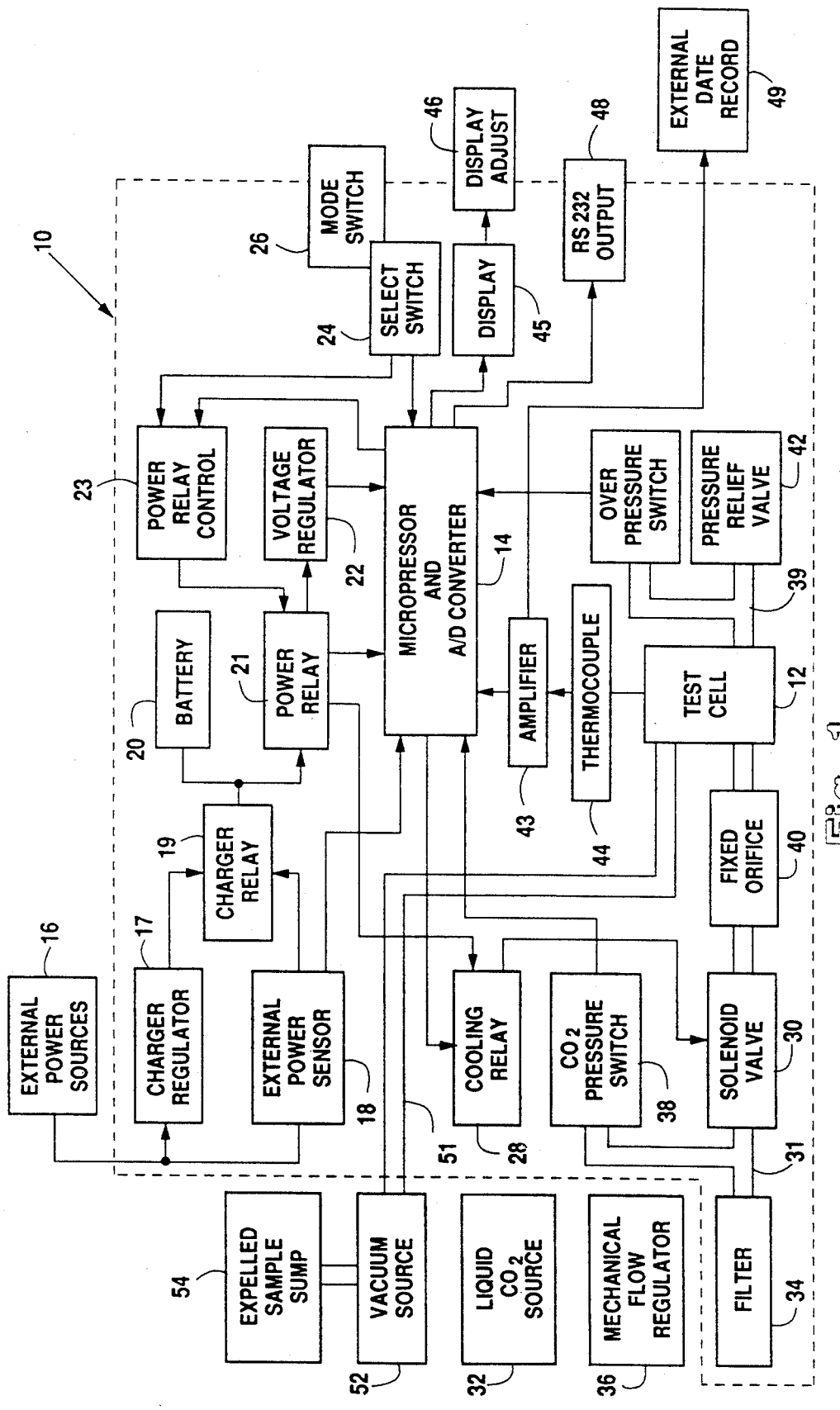
FIG. 1 is a schematic diagram of the freeze point test apparatus of the present invention.

Reference is made first to FIG. 1 for a schematic description of the primary elements of a preferred embodiment of the present invention.

The elements of the invention integral to a portable unit are included within the dotted line that represents the physical extent of freeze point test apparatus 10. The primary components of freeze point test apparatus 10 are freeze point test cell 12 and microprocessor-a/d convertor 14. Test cell 12 contains the liquid test sample (not shown) and is the element upon which all other ancillary elements work. Microprocessor-A/D convertor 14 serves as the central controlling device that runs the freeze point test, collects data, and calculates the freezing point for display to the operator.

Freeze point test apparatus 10 is configured to be attached to external power source 16. External power source 16 serves primarily to recharge battery 20. Test apparatus 10 is actually powered at all times directly by battery 20. Charger regulator 17, and external power sensor 18 work in conjunction with charger relay 19 to ensure, first that battery 20 is sufficiently charged when external power source 16 is connected, and second that there is no discharge of battery 20 if the external power source 16 fails or is disconnected. Charger regulator 17 provides an appropriate charging voltage through charger relay 19 for battery 20, while external power sensor 18 controls charger relay 19 and serves to connect or disconnect battery 20 from charger regulator 17 as required. Battery 20 is designed to handle the entire current demands of test apparatus 10. These current demands are minimal except for that current required to activate solenoid valve 30. Solenoid valve 30 would eventually drain battery 20 if external power source 16 and charger system (17, 18, 19) were not present to bring battery 20 back up to full charge.

Power is supplied to the rest of test apparatus 10 from battery 20 through power relay 21. Power relay 21 is turned on and off by power relay control 23. Power relay 21 provides power directly to cooling relay 28, to microprocessor-A/D convertor 14, and to voltage regulator 22. Voltage regulator 22 provides the alternate voltages required by microprocessor-A/D A/D convertor 14. Power relay control 23 is instructed to switch power relay 21 by microprocessor-A/D convertor 14 or by either of select switch 24 or mode switch 26. This arrangement allows the unit to either manually be turned on/off or to turn itself off after a given period of time.

Microprocessor-A/D convertor 14 provides centralized system control, data acquisition, data analyzation, and information output. The other primary component of test apparatus 10 is test cell 12. Test cell 12 contains the liquid test sample (not shown) and provides the means whereby the test sample is cooled, is allowed to warm, and is thermally tested and analyzed by the various other components of test apparatus 10.

Microprocessor 14 serves three primary functions. The first function is to start and stop the cooling of the test sample. The second function is the acquisition of thermal data during the passive warming of the test sample. The third function is the calculation and display of the freezing point based upon the thermal data acquired.

To begin the function of cooling the test sample, select switch 24 is activated to initiate microprocessor 14 and to start the flow of coolant gas. Mode and select switches 24 and 26, are designed to function in conjunction with microprocessor 14 to provide all of the test parameters required for a test run. Mode switch 26 allows the operator to step through various parameters and commands and either set parameters or initiate various preprogrammed sequence within microprocessor 14. Select switch 24 allows the operator to choose a particular parameter or execute a particular command. Mode switch 26 in the preferred embodiment, allows the operator to step through these parameters, and in conjunction with select switch 24, to instruct microprocessor 14 to utilize those parameters in an automated test sequence. The parameters that may be so chosen in the preferred embodiment are:

Calibration Low Mode—select switch 24 instructs microprocessor 14 to accept a current thermocouple value, as described below, as a low temperature value.

Calibration High Mode—Select switch 24 also instructs microprocessor 14 to accept a current thermocouple value, again as described in more detail below, as a high temperature value.

Temperature Scale Mode—Select switch 24 allows the operator to choose between degrees celsius or degrees fahrenheit.

Manual/Auto Mode—Select switch 24 instructs microprocessor 14 to allow either a manual test sequence or an automated test sequence.

Test Range Upper Mode—Select switch 24 instructs microprocessor 14 to accept an upper test range temperature value (from 0 to −50 degrees celsius in steps of 5 degrees in the preferred embodiment).

Test Range Lower Mode—Select Switch 24 instructs microprocessor 14 to accept a lower test range temperature value (from −10 degrees celsius to −70 degrees celsius in 5 degree steps in the preferred embodiment), there being a minimum 10 degree celsius difference between the upper and lower test range values.

Transmit Data Mode—Select Switch 24 instructs microprocessor 14 either to send or not to send data via RS232 output 48.

In the preferred embodiment, mode switch 26 also allows for the following commands to be initiated:

Power Control Mode—Select switch 24 instructs power relay control 23 to open or close power relay 21.

Test Mode—Select switch 24 instructs microprocessor 14 to either initiate automatic test sequence, or to take the first step of a manual test sequence.

System Status Mode—Select switch 24 steps through battery voltage, pressure, calibration information.

In the automatic mode test, the test sequence described below is stepped through automatically by microprocessor 14. In the manual test mode, select switch 24 initiates each of the steps sequentially as it is repeatedly pressed. These steps are as follows:

Step 1—Start the CO₂ sequence [liquid CO₂ flow on for set time (three seconds for example), off for set time (seven seconds for example)].

Step 2—Stop the CO₂ flow at a desired lower temperature point (cooling continues due to dry ice build-up, then warming begins).

Step 3—Start the acquisition of data (at approximately 5–10 degrees celsius below expected melting point).

Step 4—Stop the taking of data, calculating, then displaying the freezing point.

Prior to an actual test sequence operation, it is necessary to calibrate test apparatus 10 to certain known temperature values. This is essentially a calibration of thermocouple 44 with respect to voltages seen by microprocessor-A/D convertor 14. Calibration of thermocouple 44 in coordination with microprocessor 14, is achieved by pressing mode switch 26 until calibration low mode is indicated on display 45. A sample of 3-pentanone is placed in test cell 12 as a reference sample. Pressing select switch 24 initiates the calibration low test, cooling is achieved according to the procedures described in more detail below, and thermocouple readings are obtained. The temperature of the reference sample reaches a plateau in the cooling curve that is the freezing point of the reference sample. As soon as this freezing point plateau is reached, the operator presses select switch 24 again, and microprocessor 14 is instructed to accept the thermocouple reading as −40.0 degrees celsius. A similar procedure is utilized to make a second reference calibration using a higher temperature value. Mode switch 26 is pressed until calibration high mode is indicated on display 45. Thermocouple 44 is placed in a container of an ice/water combination, which is in equilibrium at 0 degrees celsius. The temperature of the ice/water combination can be confirmed with a calibrated thermometer. Once thermocouple 44 obtains a stable reading, select switch 24 is again pressed to accept the value of the thermocouple reading as 0 degrees celsius.

Microprocessor 14 controls cooling relay 28 which in turn opens (and closes) solenoid valve 30. Solenoid valve 30 is in line conduit 31 between the gas reservoir elements, described below, and test cell 12. When solenoid valve 30 is open, liquid carbon dioxide from liquid carbon dioxide source 32 is allowed to flow through mechanical flow regulator 36, filter 34, and through solenoid valve 30 towards test cell 12. The flow and pressure of this liquid carbon dioxide is monitored by CO₂ pressure switch 38. Liquid carbon dioxide flowing through solenoid valve 30 passes through fixed orifice 40 and then into test cell 12. The process whereby the expanding carbon dioxide cools the test sample is described in more detail below with respect to FIG. 2.

Over pressure switch 41 and pressure relief valve 42 are connected to test cell 12 by conduit 39 and guard against the inadvertent over pressurization of test cell 12 by the carbon dioxide after it expands into a gas.

Thermal data is obtained from the test sample within test cell 12 by means of thermocouple 44 immersed in the test sample. Thermocouple 44 is electrically connected to the a/d convertor component of microprocessor 14 by way of amplifier 43. Thermal data is continuously displayed on display 45 while the same data is being compiled by microprocessor 14. Optionally, an external data record, such as a continuous strip chart record, can be created by external data device 49, which derives a signal directly from amplifier 43. The data may also be transmitted from microprocessor 14 to an external computer or printer by way of RS232 output 48.

Once a test has been completely run, the spent test fuel may be removed from test cell 12 by way of conduit 51 by means of vacuum source 52. Vacuum source 52 is connected to expelled sample sump 54 from which the test sample can be removed at a convenient time.

Figure 2:
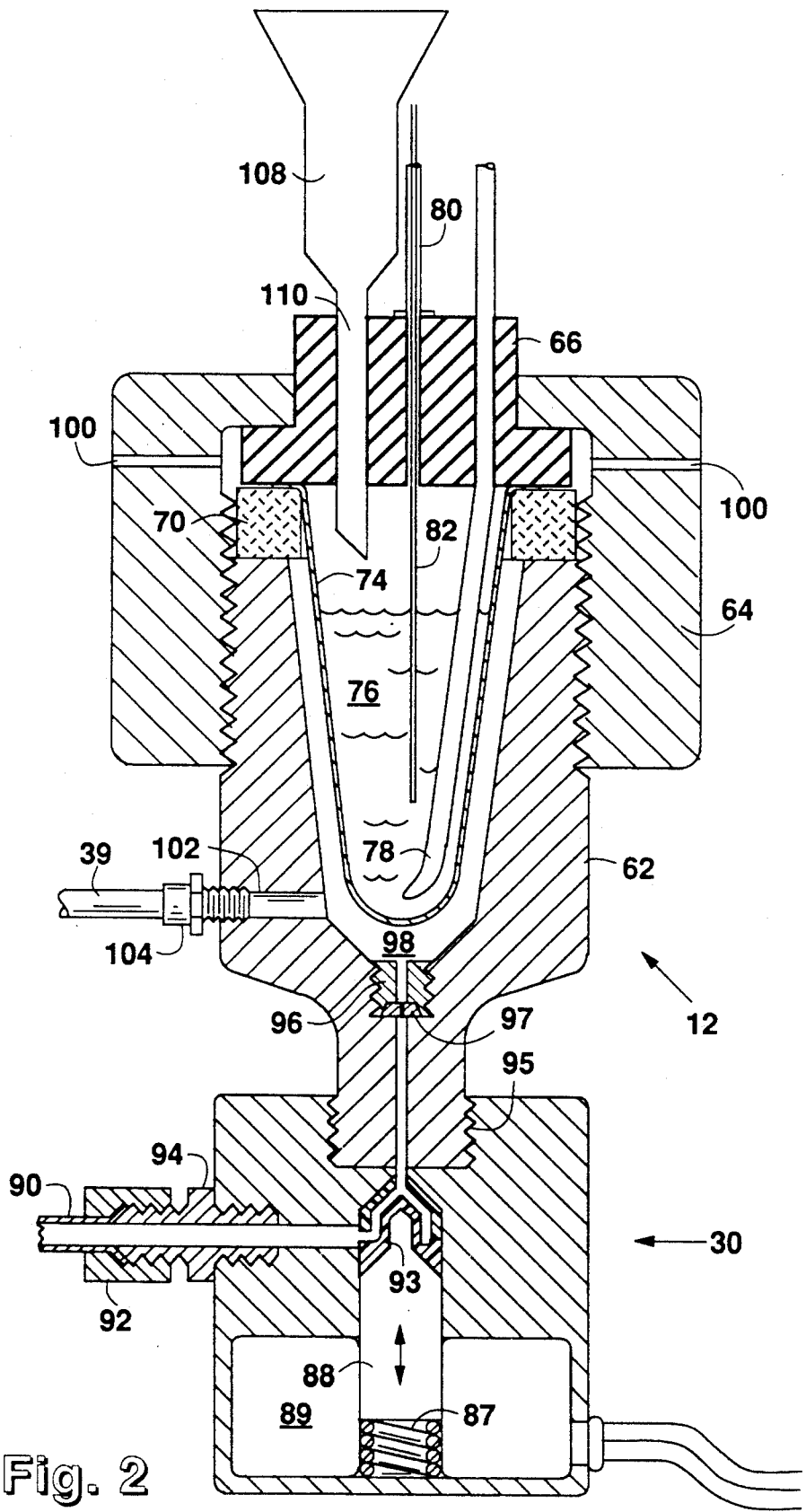
FIG. 2 is a cross section of the freeze point test cell of the present invention.

Reference is now made to FIG. 2 for a more detailed description of test cell 12 shown in FIG. 1. The main body of test cell 12 is formed by test cell base 62, and test cell top 66. Test cell top 66 is placed onto test cell base 62 and is spaced apart from test cell base 62 by means of sintered bronze collar 70. Test cell top 66 is attached to test cell base 62 by means of test cell cover 64. Test sample 76 is held within sample vial 74 which in turn is held between test cell top 66 and bronze collar 70. Test sample 76, contained within sample vial 74, fills sample vial 74 to approximately three quarters (¾) of its volume. Siphon tube 78 may be optionally inserted to extend to the base of sample vial 74 and provides a means whereby test sample 76 can be removed from sample vial 74. Thermocouple 82 passes into sample vial 74 with its insertion length controlled to an appropriate depth by outer sleeve 80. Siphon tube 78 passes upward through test cell top 66 and then to vacuum source 52 (see FIG. 1). Thermocouple 82 is connected to amplifier 43 and microprocessor-A/D convertor 14 (in FIG. 1).

Coolant is provided to test cell 12 by way of conduit 90 which is held connected to cell coolant port 94 by conduit connector nut 92. Coolant is then conducted into solenoid valve 30.

Solenoid valve 30 is a normally closed electromechnical valve comprised of solenoid core 88, valve seat 93, solenoid coils 89, and spring 87. It its unactivated state, spring 87 maintains solenoid core 88 in a position that seats valve seat 93 and closes solenoid valve 30. When current is allowed to flow through solenoid coils 89, solenoid core 88 is retracted to allow a flow of liquid carbon dioxide from cell coolant port 94 by way of valve seat 93 into cell solenoid connection 95. From cell solenoid connection 95, liquid carbon dioxide is allowed to pass through fixed orifice 97, held within orifice holder 96. Because of the increase in volume and drop in pressure across fixed orifice 97 the liquid carbon dioxide expands into a gas in expansion chamber 98. Expansion chamber 98 is below and surrounds sample vial 74. Coolant chamber dioxide is allowed to flow up and around sample vial 74 by way of a pressure release provided through sintered bronze collar 70 which on its top end is open to atmosphere by way of multiple pressure ports 100 in test cell cover 64. There are twelve of these pressure ports 100 in the preferred embodiment.

Allowing the coolant carbon dioxide to expand through fixed orifice 97 first causes the liquid carbon dioxide to change phase into the gaseous state. This change of phase provides a rapid cooling effect which ultimately reduces the temperature of the coolant carbon dioxide to a point where it begins to form solid CO2. This solid carbon dioxide builds up against sintered bronze barrier 70, and surrounds and encases sample vial 74 with solid coolant (so called "dry ice") at a very low temperature (minimum at about −78.5 degrees celsius). This solid coolant in contact with sample vial 74 provides the necessary rapid cooling of test sample 76.

Once the solid carbon dioxide has backed up sufficiently into expansion space 98, the flow must be stopped less the pressure in expansion space 98 increase and cause the opening of pressure release valve 42 (shown in FIG. 1). Over pressure switch 41 is used to sense the pressure in the cell.

However, rather than use pressure, experience has shown that a good way to operate test cell 12 is to turn the flow of carbon dioxide on and off for fixed periods of time until an adequate low temperature is achieved. This approach uses temperature as the feedback control rather than pressure. Connections to pressure relief valve 42 (shown in FIG. 1) from test cell 12 are provided by pressure relief port 102, pressure relief port connector 104, and pressure relief conduit 39. From pressure relief port 102 the pressure of test cell 12 can be monitored by microprocessor 14 through over pressure switch 41, and as described above, can be used to control the continued or discontinued cooling of test cell 12.

Test sample 76 is introduced into test cell 12 and sample vial 74, by way of sample supply funnel 108 which is fitted into test cell top 66 through sample funnel port 110, and transmits its contents directly into sample vial 74.

Test cell 12 is designed around a sample vial 74 that is sized to contain approximately 1.0 ml of sample liquid. The mass of test cell 12 is relevant only in so far as it partially determines the rate at which the passive warming of test sample 76 occurs. Brass and aluminum metal test cell components, appropriately sized to contain the 1.0 ml sample vial, have been found to bring environmental heat into the sample during warming at a suitable rate.

The necessary pressure drop and volume increase for the carbon dioxide is achieved by way of fixed orifice 97 and expansion chamber 98. The volume of expansion chamber 98 appears optimized by the establishment of an inverted conical space surrounding sample vial 74 with a thickness on the order of 0.5 mm. An optimum pressure drop is found to occur when a fixed orifice 97 on the order of 0.007–0.008 inches is used. A sapphire orifice manufactured by Richard H. Bird & Co., of Waltham, Mass., of this size, has been found suitable for the pressures and temperature encountered herein.

Liquid carbon dioxide, as used in the apparatus described above, is able to achieve temperatures in the area of −78 degrees celsius. This temperature is appropriately below the freezing point of most jet aircraft fuels. If lower freezing points are needed, it is anticipated that liquid nitrogen could replace carbon dioxide as the source of cooling for the apparatus. The cell used with such a cooling medium would be a simple design where the vial would be surrounded by a small portion of introduced liquid nitrogen. The cell vial, top, and cover geometry would be essentially the same as described for the above carbon dioxide coolant device.

What components of test apparatus 10 are included in a package, and what are not, could vary. The pressurized gas source components, 32–36 in FIG. 1, could be incorporated into a portable package if desired by utilizing a small pressurized gas cylinder for source 32, capable of providing enough gas for one or perhaps two test runs. It would be a simple matter of switching out an expanded gas cylinder with a new one to continue the use of the apparatus.

Removal of test sample 76 from sample vial 74 could likewise be achieved either through a standard laboratory vacuum source 52 and sample sump 54, or could be achieved by using a simple hand operated bulb vacuum device for source 52 connected in line with a single sample size container for sump 54. Any suitable device for drawing out 1.0 milliliters of liquid sample can be utilized in the embodiment.

Figure 3:
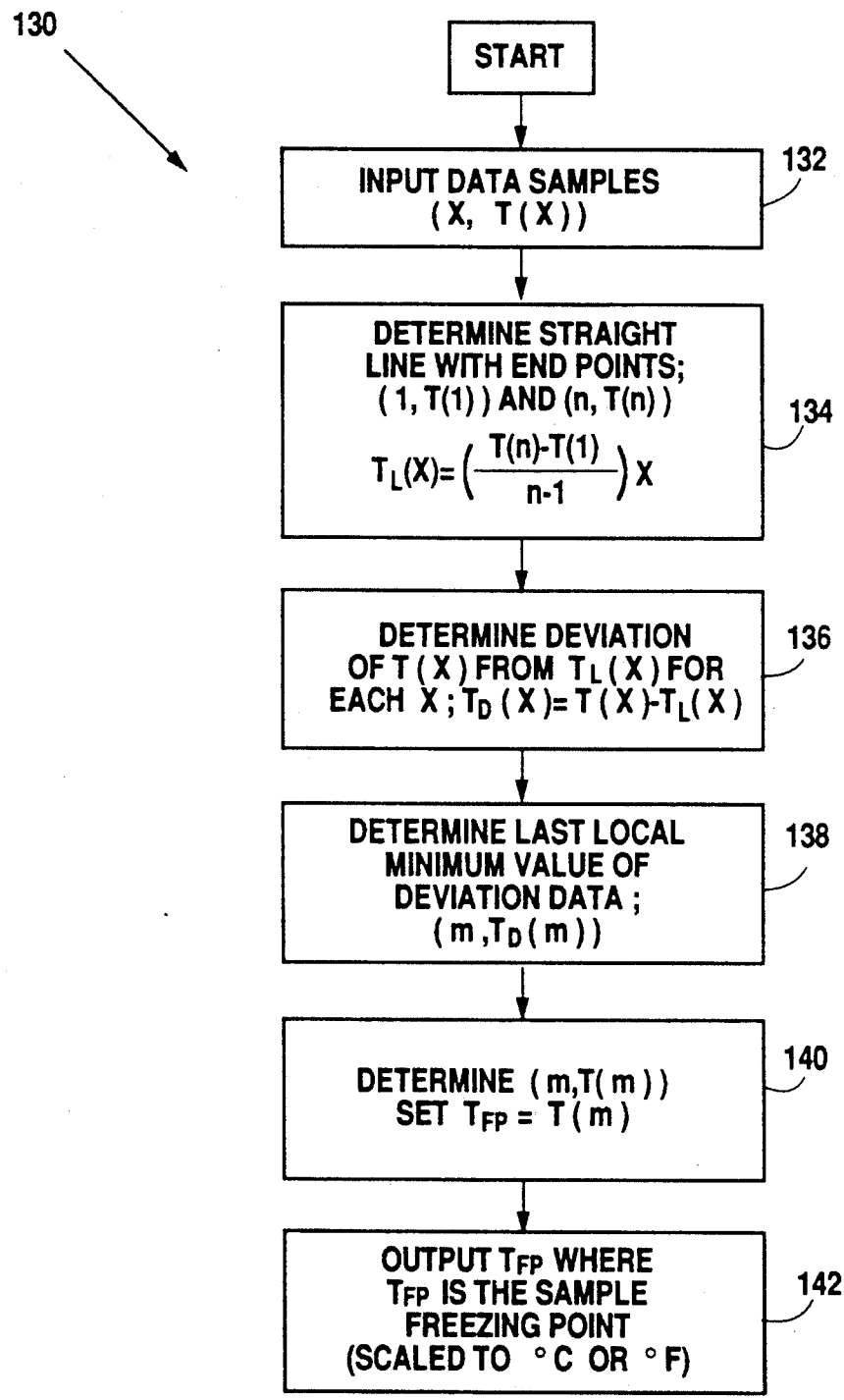
FIG. 3 is a flow chart of the freeze point determination method described by the present invention.

Reference is now made to FIG. 3 for flow chart 130 showing the primary steps through which microprocessor 14 (shown in FIG. 1) moves in the collection and analysis of the sample data and the calculation of the sample freeze point. After the sample has cooled below an expected freezing point and the passive warming is allowed to begin, the method described in flow chart 130 is initiated. Data sample input step 132 is the process of collecting discrete thermocouple readings through a low pass filter, (not shown), digitizing these readings with the A/D convertor component of microprocessor 14, and associating them with periodic time intervals at which they occur, giving an ordered pair $(X_1 T(x))$. An array of thermocouple readings equally spaced in time, or over equal time intervals is created. The number taken depends upon an operator selected temperature range (described above) designed to encompass the expected freezing point of the sample from which the actual freezing point can be determined. This range should be sufficient to allow for any expected deviations from the predicted freezing point value and is typically a 10 degree celsius range minimum.

Microprocessor 14 then proceeds to straight line calculation step 134 that projects a linear set of increasing temperature values that contain the end points of the range. The end points of the range are specified generally as $(1, T(1))$ and $(n, T(n))$. Any particular point in the range on the data sample warming curve is specified as $(x, T(x))$. The straight line passing through the end points has the general equation, $T_L(x) = [(T(n) - T(1)/(n-1)]x + T(1)$.

Deviation calculation step 136 is the process of determining the deviation $T_D(x)$ of each sample value $T(x)$, from each corresponding linear value $T_L(x)$. This deviation is determined for every sample point, x. These deviation values, $T_D(x)$, are equal to the difference between each $T(x)$ and $T_L(x)$.

With this set of deviation data, microprocessor 14 continues to step 138 and works backwards through the deviation data to find the last local minimum in the deviation curve (the last local maximum negative deviation value). This process is accomplished by comparing $T_D(x)$ for a given x with $T_D(x)$ for the previous x. Once a trend is established, a local minimum value $T_D(m)$ can be determined. This last local minimum method insures that other changes in the temperature curve do not result in erroneous indications of a freeze point. During the determination of a last local minimum of the deviation curve in step 138, two forms of numerical "filtering" occur which help establish a trend, and which eliminate anomalies in the data. The first of these numerical filters, establishes some minimum deviation between data values before microprocessor 14 acknowledges a positive or negative trend. The second of these numerical filters establishes a maximum deviation value that instructs microprocessor 14 to dispose of data points that differ from an adjacent data point by more than some maximum amount.

Finally, after a last local minimum $T_D(m)$ is determined by step 138, the process proceeds to freeze point temperature determination step 140. $T(x)$ for $X = m$ is found from the stored sample data and is determined to be the freeze point $T_{FP}$. Step 142 involves scaling the thermal data value $T_{FP}$ and converting to a freezing point value in degrees celsius or fahrenheit. Output freezing point temperature step 142 provides the test operator with the test results at display 46.

Figure 4:
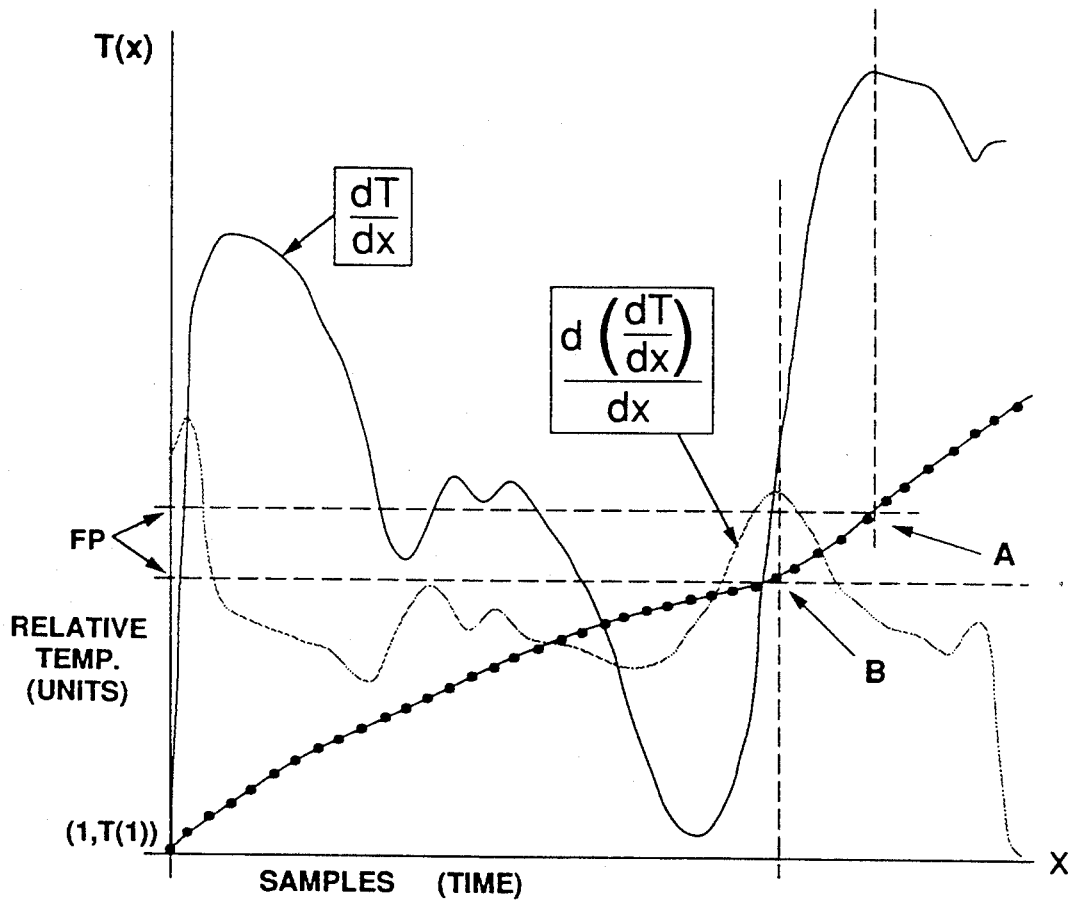
FIG. 4 is a temperature versus time graph for methods that utilize first and second derivatives to determine the inflection point of a warming curve.
Figure 5:
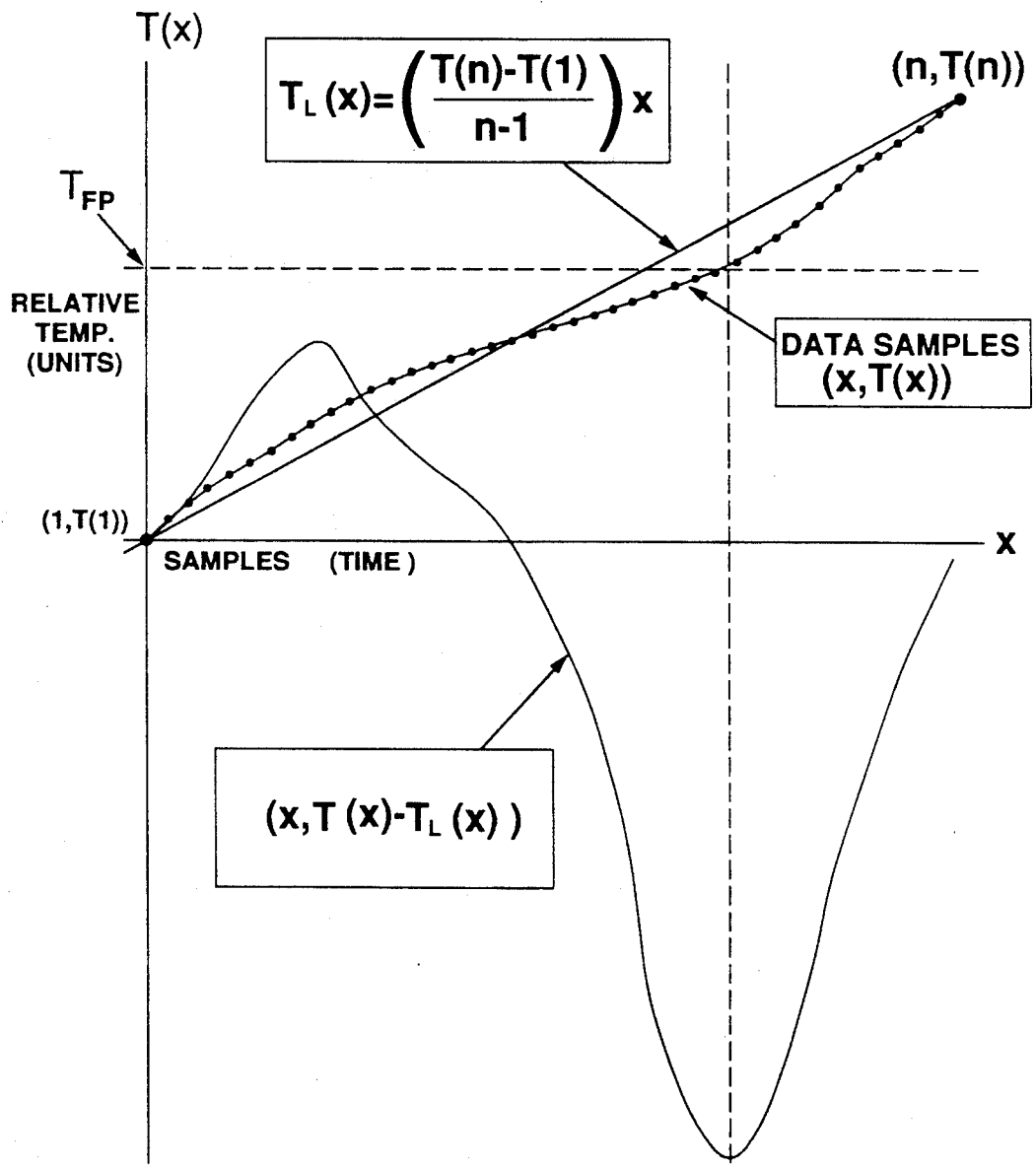
FIG. 5 is a temperature versus time graph for the method of determining the freezing point described by the present invention.

FIG. 5 is a graphic representation of the steps and analysis that are described in flow chart 130 of FIG. 3. The graph is a plot of periodic samples over time along the x axis versus relative temperature units along the $T(x)$ axis. The solid curve broken by periodic points is representative of the temperature data samples of the warming curve collected by the test apparatus. This curve is labeled as "Data Samples $(x, T(x))$". As with the similar curve in FIG. 4, this data sample curve is a portion of the warming curve that the temperature of the substance proceeds along as the phase change from a solid to a liquid state occurs. The vague plateau in the center of the curve represents the time period over which heat being absorbed by the sample is utilized in changing phase rather than in a significant temperature change as is seen above and below the phase change plateau. The so called "knee of the curve", where the temperature change is again more prominent, is the general location of the sought after freezing point of the substance.

The method described herein begins by projecting a linear temperature change with end points being the first data sample and the final data sample in the range selected. The range for these data samples is selected to appropriately encompass the freezing point plateau to be analyzed. The straight line between the end points of the data sample range has the equation $T_L(x) = mx + b$, where m is the slope of line and b is the $T(x)$ intercept of the line. This is a general linear relationship. As stated previously, the specific equation of the line is $T_L(x) = [(T(n) - T(1)/(n-1)]x + T(1)$.

The next step in the method is a determination of the deviation of the data sample curve from the straight line drawing between its end points. As can be seen in general from the solid curve draw in the graph in FIG. 5, this deviation is initially zero, increases to a positive value, is zero again, decreases to a negative value, and finally returns to zero at the terminus point. An amplified plot of this deviation curve is represented by the solid line labeled as $(x, T(x) - T_L(x))$. From this curve, it can be seen that there is a point at which the warming curve has its greatest deviation from the linear curve drawn between the end points. In this example, this greatest deviation is the last local minimum found on the curve. It is this last local minimum that has been found to identify the freezing point of the substance. The last local minimum is used to determine this value so as to eliminate the lower independent freezing points of the various components that might exist in the substance. In other words, the freezing point of a substance in general is, for all practical purposes, the highest freezing point of any element within the substance. The freezing points of elements which are lower are not so relevant for practical purposes. The last local minimum method, therefore, searches for the last, warmest, point at which this deviation occurs.

As mentioned above, this method of numerically analyzing the warming curve approaches both practically and theoretically an analysis of the second derivative of the warming curve. This method, however, achieves a determination of the freezing point without the complex differentiating electronics and computer calculations that a determination of the second derivative would require. This method also is less likely to mistake false maximum on the second derivative curve as indicative of freezing point values.

While the foregoing discussion of the present invention has described the apparatus and the process in relation to certain preferred embodiments, and specific details have been disclosed for the purpose of illustration, it will be apparent to those skilled in the art that the invention is open to additional embodiments and that the details of the descriptions above could be altered considerably without departing from the basic principles of the invention.

I claim:

1. A device for determining the freezing point of a substance, comprising:
   means for cooling said substance to a temperature below a range within which said freezing point of said substance is predicted to be, said means for cooling said substance comprising:
   a pressurized gas reservoir containing a gas under sufficient pressure as to allow said gas, upon expanding to atmospheric pressure, to absorb heat from a sample of said substance;

a test cell, said test cell defining a volume within which to contain said sample of said substance, said test cell having an inlet for said expanding gas, said test cell further defining a volume within which to allow a flow of said expanding gas, said expanding gas being in thermal contact with said sample of said substance;

a gas conduit, said gas conduit connecting said pressurized gas reservoir to said inlet of said test cell; and an orifice positioned at said inlet of said test cell, said orifice capable of controlling the rate of expansion of said expanding gas;

means for passively allowing said substance to warm to a temperature above said range within which said freezing point is predicted to be;

means for obtaining a time sequential plurality of temperature measurements of said substance, each of said temperature measurements associated with one of a plurality of sequential time intervals, there being a first and a last temperature measurement, said first temperature measurement being made at a lowest temperature value in said range and said last temperature measurement being made at a highest temperature value in said range; and means for determining an occurrence of a phase change in said substance from said time sequential plurality of temperature measurements, said phase change being indicative of said freezing point of said substance.

2. The device of claim 1 wherein said means for passively allowing said substance to warm, comprises a thermal mass surrounding and in thermal contact with said substance, said mass capable of transferring heat from an open, atmospheric environment surrounding said mass into said substance, said thermal mass comprising a mass of a configuration and composition that provides thermally conductive characteristics appropriate for a constant heat flux from said open, atmospheric environment into said substance.

3. The device of claim 1 wherein said means for obtaining a sequential plurality of temperature measurements of said substance, comprises:

a thermocouple positioned within said substance, said thermocouple capable of providing a voltage signal directly related to a temperature of said substance;

an analog to digital convertor capable of converting said thermocouple signal to a digital value proportional to said thermocouple signal; and a microprocessor having a timing device, said microprocessor capable of sequentially sampling said digital value from said analog to digital convertor, said sequential sampling occurring at regular time intervals of preselected duration.

4. The device of claim 1 wherein said means for determining an occurrence of a phase change, comprises a microprocessor having a timing device, said microprocessor capable of storing said sequential temperature measurements in conjunction with values representative of said associated time intervals, determined by said timing device, by which said temperature measurements were made, said microprocessor further being capable of identifying a non-linearity in said sequential plurality of temperature measurements, said non-linearity being indicative of said phase change in said substance.

5. The device of claim 1 wherein said test cell comprises:

a cell base, said cell base including said inlet of said test cell, said cell based partially defining a lower boundary of said volume within which to allow said flow of said expanding gas;

a cell top, said cell top partially defining an upper boundary of said volume within which to allow said flow of said expanding gas, said cell top comprising:

a sample vial, said sample vial partially defining said upper boundary of said volume, said sample vial capable of containing a sample of said substance;

a sample vial top, said sample vial top configured to cover and close said sample vial, said sample vial top having a first, a second, and a third port therethrough;

a thermocouple, said thermocouple passing through said first port of said sample vial top and into an interior space defined by said sample vial wherein said thermocouple may be emersed within a sample of said substance placed within said sample vial;

a siphon tube, said siphon tube placed through said second port in said sample vial top, said siphon tube extending into an interior space defined by said sample vial wherein said siphon tube may be positioned so as to terminate at a lowest point in said sample vial. Wherein said siphon tube may serve to draw a sample of said substance from said sample vial;

a sample funnel, said sample funnel passing through said third port in said sample vial top, said sample funnel configured to allow the placement of a sample of said substance within said sample vial;

a sintered metal collar, said metal collar positioned between said cell top and said cell base in a manner wherein said metal collar partially defines an upper boundary of said volume with said sintered metal collar serving to communicate said volume with an area exterior to said cell base and said cell top;

a cell cover, said cell cover serving to connect said cell base to said cell top with said sintered metal collar positioned between, said cell cover further defining said area exterior to said cell base and said cell top, said cell cover having a plurality of passages formed therein, wherein said area exterior to said metal collar is communicated with an area exterior to said cell cover, said cell cover further serving to act as a thermal mass to slow a warming of said sample.

6. The device of claim 5, wherein said sample vial is configured in the form of an inverted cone and defines said volume within which to allow said flow of said expanding gas as a similarly configured inverted cone.

7. The device of claim 5, wherein said cell base is made of brass; said sample vial top is made of acetal material; and said cell cover is made of aluminum.

8. The device of claim 5, wherein said cell base further comprises an over pressure port, wherein said expanding gas may be monitored and released if a pressure of said expanding gas exceeds a predetermined value.

9. A method for determining the freezing point of a substance, comprising the steps of:

cooling said substance to a temperature below a predicted freezing point of said substance, said step of cooling said substance comprising the steps of:

containing a gas under sufficient pressure as to allow said gas, upon expanding to atmospheric pressure, to absorb heat from said substance;

containing said substance in a test cell, said test cell having an inlet for said expanding gas, said test cell further being capable of containing a volume of said expanding gas, said expanding gas being in thermal contact with said substance;

conducting said pressurized gas to said inlet of said test cell; and controllably expanding said pressurized gas by passing said gas through an orifice positioned at said inlet of said test cell;

passively allowing said substance to warm to a temperature above said predicted freezing point of said substance;

obtaining a time sequential plurality of temperature measurements of said substance, each of said temperature measurements associated with one of a plurality of sequential time intervals, said sequential plurality of temperature measurements having a first and a last temperature measurement, said first temperature measurement being made at a lowest temperature value in said range and said last temperature measurement being made at a highest temperature value in said range; and determining an occurrence of a phase change in said substance from said time sequential plurality of temperature measurements, said phase change being indicative of said freezing point of said substance.

10. The method of claim 9 wherein said step of passively allowing said substance to warm, comprises surrounding said substance with a thermal mass in thermal contact with said substance, said mass capable of transferring heat from an open, atmospheric environment surrounding said mass into said substance, said thermal mass comprising a mass of a configuration and composition that provides thermally conductive characteristics appropriate for a constant heat flux from said open, atmospheric environment into said substance.

11. The method of claim 9 wherein said step of obtaining a sequential plurality of temperature measurements of said substance, comprises the steps of:

positioning a thermocouple within said substance, said thermocouple providing a voltage signal directly related to a temperature of said substance;

inputting said thermocouple signal to an analog to digital convertor and outputting a digital value proportional to said thermocouple signal;

sequentially sampling said digital value output by said analog to digital convertor, said sequential sampling occurring at regular time intervals of preselected duration; and storing each said digital value in conjunction with a time value indicative of said time interval at which said digital value was sampled.

12. The method of claim 9 wherein said step of determining an occurrence of a phase change, comprises the steps of:

storing said temperature measurements and storing said time correspondent linear set of sequential temperature values projected between said first temperature measurement and said last temperature measurement;

identifying a non-linearity in said sequential plurality of temperature measurements, said non-linearity being indicative of said phase change in said substance.

* * * * *